US00PP27934P2

(12) United States Plant Patent
Moore

(10) Patent No.: US PP27,934 P2
(45) Date of Patent: Apr. 25, 2017

(54) ***BUDDLEJA* PLANT NAMED 'PMOORE12'**

(50) Latin Name: ***Buddleja alternifolia*×*caryopteridifolia***
Varietal Denomination: Pmoore12

(71) Applicant: Peter R. Moore, Stockbridge (GB)

(72) Inventor: Peter R. Moore, Stockbridge (GB)

( * ) Notice: Subject to any disclaimer, the term of this patent is extended or adjusted under 35 U.S.C. 154(b) by 132 days.

(21) Appl. No.: 14/545,883

(22) Filed: Jun. 30, 2015

(51) Int. Cl.
*A01H 5/00* (2006.01)

(52) U.S. Cl.
USPC ..... Plt./242

(58) Field of Classification Search
USPC ..... Plt./226, 242
See application file for complete search history.

(56) References Cited

PUBLICATIONS

PLUTO: Plant variety database, Dec. 29, 2016, citation for 'pmoore12'. 1 page.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Buddleja alternifolia*×*caryopteridifolia* plant named, 'Pmoore12', that is characterized by its compact and bushy plant habit, its sterile flowers that bloom on new growth, its long and repeating bloom season, and its cold hardiness at temperatures as low as −25° C.

2 Drawing Sheets

Botanical classification: *Buddleja alternifolia*×*caryopteridifolia.*

Variety denomination: 'Pmoore12'.

BACKGROUND OF THE INVENTION

The present invention relates to a new and distinct cultivar of *Buddleja alternifolia*×*caryopteridifolia* (syn. *Buddleja*× *pikei*) and will be referred to hereafter by its cultivar name, 'Pmoore12'. 'Pmoore12' is a new shrub grown for use as an ornamental landscape plant.

The new cultivar of *Buddleja* is a selection from an ongoing breeding program conducted by the Inventor in Longstock, England with the objective of creating new cultivars of *Buddleja* with sterile flowers that do not set seed.

The new variety of *Buddleja*, 'Pmoore12', arose from a cross made in 2008 between an unnamed proprietary plant (not patented) of *Buddleja alternifolia* from the Inventor's breeding program as the female parent and an unnamed proprietary plant (not patented) of *Buddleja caryopteridifolia* from the Inventor's breeding program as the male parent. 'Pmoore12' was selected from amongst the resulting seedlings as a single unique plant in 2011.

Asexual propagation of the new cultivar was first accomplished by the Inventor using stem cuttings in 2011 in Longstock, England. Asexual propagation by tissue culture and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pmoore12' as a unique cultivar of *Buddleja.*

1. 'Pmoore12' exhibits a compact and bushy plant habit.
2. 'Pmoore12' exhibits sterile flowers.
3. 'Pmoore12' exhibits flowering on new wood.
4. 'Pmoore12' exhibits a long and repeating bloom season; blooming on new wood from early to late summer in England.
5. 'Pmoore12' exhibits cold hardiness at temperatures as low as −25° C. (−13° F.).

The female parent differs from 'Pmoore12' in having a larger more pendulous plant habit, in flowering only on the previous years' growth, and in having fertile flowers that produce seed. The male parent differs from 'Pmoore12' in having a larger more spreading plant habit, in flowering only on the previous years' growth, and in having fertile flowers that produce seed. 'Pmoore12' can be compared to the *Buddleja alternifolia* cultivar 'Argentea' (not patented). 'Argentea' differs from 'Pmoore12' in being larger in overall size, in having foliage that is silvery green in color, in having a non-repeating bloom season, and in having fertile flowers that produce seed.

BRIEF DESCRIPTION OF THE DRAWINGS

The accompanying colored photographs illustrate the overall appearance and distinct characteristics of the new *Buddleja*. The photographs were taken of a 20 month-old plant as grown in a greenhouse in a 17-cm container in Boskoop, The Netherlands.

The photograph in FIG. 1 provides a side view of the overall plant habit of 'Pmoore12' in bloom.

Figure 1:
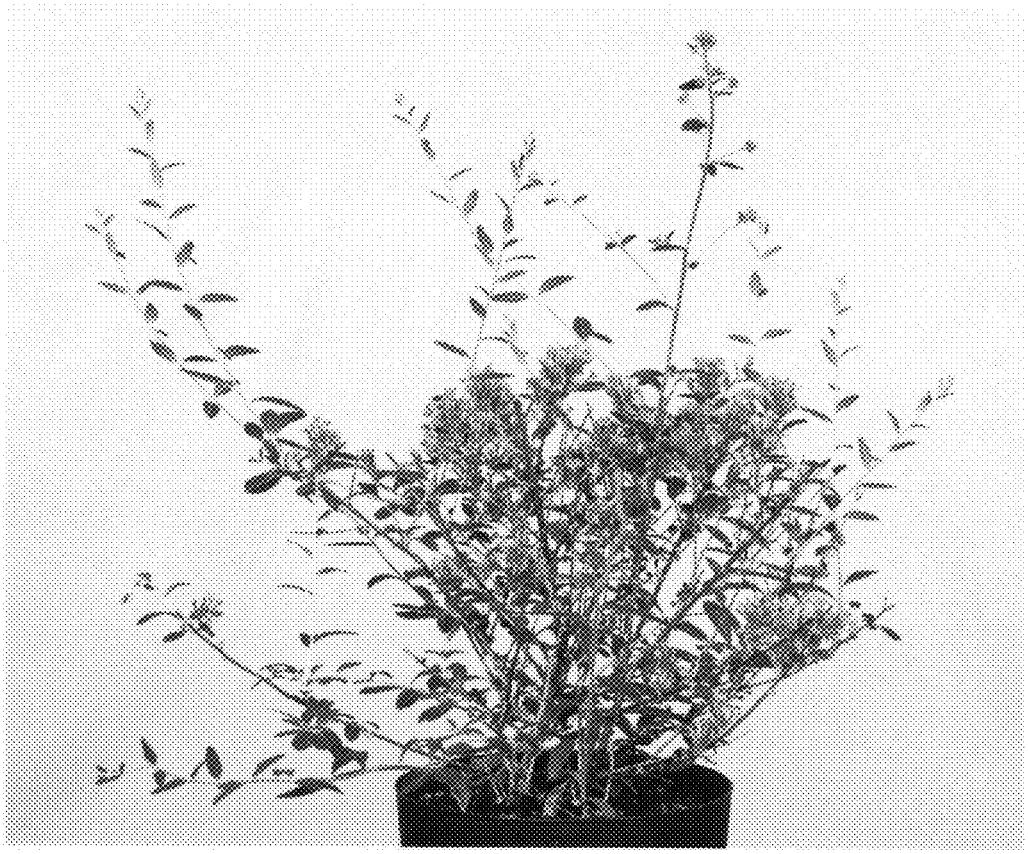
Figure 2:
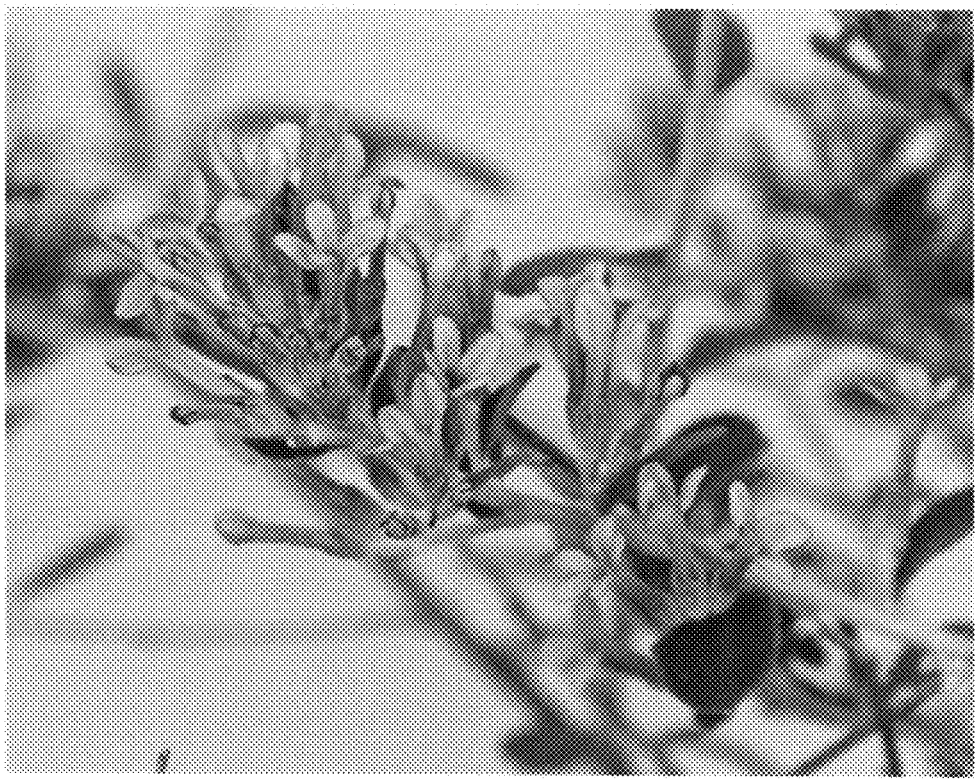

The photograph in FIG. 2 provides a close-up view of the inflorescences of 'Pmoore12'.

Figure 3:
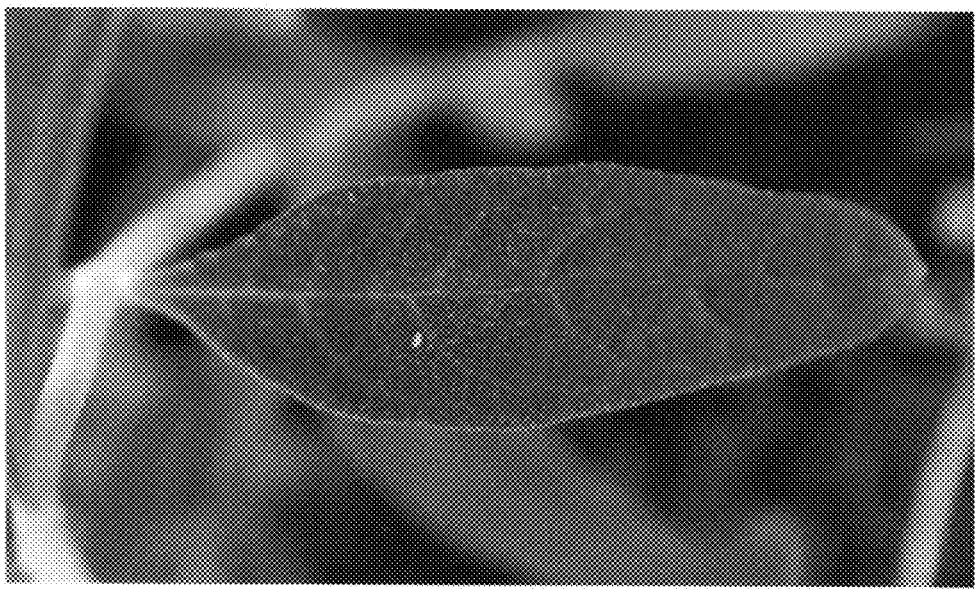

The photograph in FIG. 3 provides a close-up view of the foliage of 'Pmoore12'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of 20 month-old plants as grown in a greenhouse in 17-cm containers in Boskoop, The Netherlands. Plants were grown under average day temperatures of 15° C. to 23° C. and average night temperature of 3° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from early to late summer in England.

*Plant type*.—Deciduous shrub.

*Plant habit*.—Compact and bushy.

*Plant size*.—An average of 39 cm in height and 57.5 cm in width as grown in a 17-cm container, an average of 120 cm in height and 80 cm in diameter when 2 years in age as grown in the landscape.

*Hardiness*.—At least to U.S.D.A. Zone 5.

*Diseases and pests*.—Similar susceptibility and resistance to diseases and pests as other *Buddleja alternifolia* cultivars has been observed.

*Root description*.—Fibrous and fine.

Growth and propagation:

*Propagation*.—Tissue culture (preferred) and stem cuttings.

*Root initiation*.—An average of 20 days at soil temperatures of 18° C.

*Root development*.—An average of six weeks at air temperatures of 20° C. to finish a young plant.

*Growth rate*.—Moderate.

Stem description:

*Shape*.—Rounded.

*Stem color*.—N144B, mature bark N199C to N199D.

*Stem strength*.—Strong.

*Stem size*.—An average of 18 cm in length and 2 mm in diameter.

*Stem surface*.—Very slightly glossy and densely covered with woolly floccose hairs 192D in color.

*Stem aspect*.—Lateral stems held at an average angle of 45° to main stems.

*Branching*.—Freely branches with lateral branches growing from base and main stems, an average of 36 lateral branches.

Foliage description:

*Leaf shape*.—Elliptic to narrowly obovate.

*Leaf division*.—Simple.

*Leaf base*.—Acuminate to attenuate.

*Leaf apex*.—Acute to nearly obtuse.

*Leaf fragrance*.—None.

*Leaf venation*.—Pinnate, color; upper surface 138B and lower surface 193A.

*Leaf margins*.—Entire, occasionally with 1 to 2 coarse teeth.

*Leaf arrangement*.—Alternate to nearly opposite.

*Leaf attachment*.—Petiolate.

*Leaf surface*.—Upper surface; smooth and moderately glossy and lower surface; dull, both surfaces moderately to densely covered with woolly floccose hairs, less than 1 mm in length and 192D in color.

*Internode length*.—An average of 2.0 cm.

*Leaf size*.—An average of 3.6 cm in length and 1 cm in width.

*Leaf quantity*.—An average of 12 per stem.

*Leaf color*.—Young upper surface; 137B, young lower surface; 192A, mature upper surface; 137A, mature lower surface; a blend between 138B and 191A.

*Petioles*.—An average of 2 mm in length and 1 mm in diameter, 193A in color, pubescent surface.

Inflorescence description:

*Inflorescence type*.—Compound terminal and axial panicles.

*Inflorescence size*.—An average of 5.1 cm in height and 3.1 cm in diameter.

*Flower fragrance*.—Moderate, typical *Buddleja alternifolia* scent.

*Lastingness of flowers*.—An average of 10 days with about 30% of flowers in bloom at one stage, self-cleaning.

*Flower buds*.—Narrowly spathulate in shape, an average of 8 mm in depth and 2 mm in diameter, N77C in color with basal portion 138B.

*Flower aspect*.—Outward and upright.

*Flower quantity*.—An average of 31 flowers per inflorescence.

*Flower type*.—Single, salverform.

*Flower size*.—An average of 9 mm in diameter and 12 mm in depth.

*Peduncles*.—An average of 3.9 cm in length and 2 mm in diameter, held at an average angle of 0° to lateral stem, N144B in color, moderately strong, pubescent surface.

*Pedicels*.—An average of 3 mm in length and 0.75 mm in diameter, held at an average angle of 225° to peduncle, N144B in color, moderately strong, pubescent surface.

*Calyx*.—Campanulate in shape, an average of 5 mm in depth and 3 mm in diameter.

*Sepals*.—4, ovate and fused into a campanulate overall shape, entire margin, acute apex, lower 80% fused, and average of 5 mm in length and 0.5 mm in width, color; upper surface when opening and when fully open 143A, lower surface when opening and when fully open 138B, both surfaces dull and densely covered with floccose hairs, less than 1 mm in length and 192D in color.

*Petals*.—4, occasionally 5, lower 70% fused into tube, free parts ovate to obovate in shape, entire margin, obtuse apex, an average of 1.3 cm in length and 2 mm in width, outer and inner surface is slightly velvety and glabrous, color; upper surface when opening 84A to 84B with tube 77B suffused with 35C towards the base, lower surface when opening 84B with tube suffused 173B towards the base, upper surface when fully opened 84B with tube suffused with 21B to 21D towards the base, lower surface when fully opened 84B with tube suffused with 173B towards the base, color not fading.

Reproductive organs:

*Gynoecium*.—1 pistil, deformed and hardly visible an average of 2 mm in length, style; an average of 0.1 mm in length and 144A in color, stigma is narrow club-shaped and 144A in color, ovary is 143A in color.

*Androcoecium*.—Not detected.

*Fruit and seed*.—Flowers are sterile, no seeds are produced.

It is claimed:

1. A new and distinct cultivar of *Buddleja* plant named 'Pmoore12' as herein illustrated and described.

* * * * *